United States Patent [19]

Granatek et al.

[11] 4,177,199

[45] Dec. 4, 1979

[54] SILVER SALTS OF PHOSPHANILIC ACID

[75] Inventors: Edmund S. Granatek, Syracuse; Frank D. Ruva, Auburn; Frederick L. Grab, Fayetteville, all of N.Y.

[73] Assignee: Bristol-Myers Company, New York, N.Y.

[21] Appl. No.: 968,315

[22] Filed: Dec. 11, 1978

[51] Int. Cl.$^2$ .............................................. C07F 1/10
[52] U.S. Cl. .................................... 260/430; 424/290
[58] Field of Search ........................................ 260/430

[56] References Cited

U.S. PATENT DOCUMENTS 2,328,358   8/1943   Pike .................................. 260/430 X

OTHER PUBLICATIONS

JACS 63, 2137 (1941).
JACS 74, 753–754 (1952).

*Primary Examiner*—Helen M. S. Sneed
*Attorney, Agent, or Firm*—Herbert W. Taylor, Jr.

[57] ABSTRACT

Monosilver phosphanilate and disilver phosphanilate were prepared and found to be potent antibacterial agents, especially against strains of Pseudomonas, suitable for use in the topical therapy of burns.

12 Claims, No Drawings

SILVER SALTS OF PHOSPHANILIC ACID

BACKGROUND OF THE INVENTION

1. Field of the Invention

The present invention provides the silver salts of phosphanilic acid which are potent antibacterial agents especially against strains of Pseudomonas and thus useful for topical application in the therapy of burns.

2. Description of the Prior Art

Silver sulfadiazine is an antibacterial agent used in the topical treatment of burns. It has disadvantages of sulfonamide sensitivity and the need to monitor sulfonamide concentrations in the bloodstream to prevent renal dysfunction and crystalluria when the burned area covers more than twenty percent of the total body surface. It has also been reported to be effective in the topical treatment of skin ulcers and herpes virus. It is of particular value in burn therapy because of its potent antibacterial activity against infections by strains of Pseudomonas which occur often in such patients.

Silver Sulfadiazine was apparently first disclosed in U.S. Pat. No. 2,422,688 and see also U.S. Pat. Nos. 3,761,590 and 3,792,161. Various complexes are described in U.S. Pat. Nos. 2,536,095 and 2,629,682. Silver derivatives of pyrimidines and purines are disclosed in Farmdoc 69657R. Other preparations and uses are disclosed in Chemical Abstracts, 81, 158672c, Farmdoc 04862X, U.S. Pat. No. 4,020,150, Farmdoc 70776Y and Farmdoc 39520A. For combinations with other, novel metal salts of sulfadiazine, e.g. zinc and cerium, see U.S. Pat. Nos. 4,088,754, 4,078,058 and Farmdoc abstracts 63047Y, 73999X and 04160A.

Silver zinc allantoinate is disclosed in U.S. Pat. No. 3,856,805 as a new compound with bactericidal and wound-healing properties. Silver allantoinate has been described for the treatment of burns in U.K. Pat. No. 1,346,544. See also U.S. Pat. Nos. 3,830,824, 3,830,825 and 3,830,908 which broaden the concept to include other acids and metals such as zinc.

Silver sulfadiazine is marketed as "SILVADENE" Cream by Marion Laboratories Inc., Kansas City, Mo.; see pages 1073-1074 of the 32nd edition of Physicians' Desk Reference published by Medical Economics Company, Oradell, N.J. (1978). Its preparation is described in Farmdoc abstract 39520A. The in vitro antibacterial activity of silver sulfadiazine has been reported, for example, by Carr et al., Antimicrobial Agents and Chemotherapy, 4(5), 585-587 (1973).

Current Science (India), 16, 223-225 (1947) reports the in vitro antibacterial activity of phosphanilic acid and some of its derivatives against *E. coli, S. aureus, Typhi murium, C. xerosis* and Boyd II.

Current Science (India), 17, 125-6 (1948) reports blood level and toxicity studies with phosphanilic acid in laboratory animals. Their results indicated poor absorption and low toxicity.

H. Bauer, J. Amer. Chem. Soc., 63, 2137-2138 (1941) reported a synthesis of phosphanilic acid as have others such as G. O. Doak et al., J. Amer. Chem. Soc., 74, 753-754 (1952). A few salts are also described in these publications.

J. Pharmacol. Exp. Therap., 74, 163-173 (1942) reports the testing of various sulfonamides, sulfones and related phosphorus compounds against experimental tuberculosis. They found that phosphanilic acid had good tubercularstatic activity in vitro but no effect in vivo, presumably due to low blood concentrations of phosphanilic acid.

Chemical Abstracts, 55, 2883 g (1961) [from Texas Repts. Biol. and Med., 18, 379-394 (1960)] reports that phosphanilic acid had some protective effect when tested in white mice against a standardized infection produced by intravenous injection of the yeast phase of *Histoplasma capsulatum*.

Antibiotics and Chemotherapy, 3, 256-264 (1953) report the in vitro activity of some aromatic phosphonic and phosphinic acids against a variety of bacterial species. Phosphanilic acid was reported as being generally the most active of the compounds tested. Its activity approached that of sulfathiazole when compared on a molar basis and its antibacterial spectrum was similar to that of sulfanilamide. It was also stated that a later paper would report in detail the findings that phosphanilic acid was effective in vivo in mice infected with *S. typhosa, Ps. fluorescens* and *Plasmodium berghei*.

U.S. Pat. No. 3,159,537 discloses the potentiation of various tetracycline antibiotics by admixture with (or salt formation with) various organic oxyphosphorous compounds, including phosphanilic acid.

Ciencia (Mexico), 17, 71-73 (1957) reports studies of the in vitro synergism of mixtures of phosphanilic acid with neomycin or streptomycin on various clinically isolated strains of Salmonella, Shigella and Proteus as well as coliform bacteria capable of inducing fermentation of lactose. The combination of phosphanilic acid and neomycin showed synergism against Salmonella, Proteus and the coliform bacteria. With Shigella, however, there was only slight synergism for low concentrations and only an additive effect, or no effect, at medium and high concentrations.

It was the object of the present invention to provide improved agents for burn therapy which, in addition, lacked the disadvantage of silver sulfadiazine.

SUMMARY OF THE INVENTION

The objectives of the present invention were achieved by the provision, according to the present invention, of silver salts of phosphanilic acid and particularly of monosilver phosphanilate and disilver phosphanilate.

There is further provided by the present invention the process for preparing a silver salt of phosphanilic acid which comprises mixing, preferably at room temperature, an aqueous suspension of phosphanilic acid with an aqueous solution containing approximately either one or two moles of silver nitrate per mole of phosphanilic acid to form a mixture which is then mixed with a water-miscible organic solvent, preferably acetone and preferably by slow addition to the organic solvent with the optional addition of a small amount of ammonium hydroxide, to precipitate the desired product.

In a typical formulation a salt of the present invention is incorporated, preferably in micronized form in a water-miscible cream which is preferably a hypoallergenic cream at a concentration, for example, in the range of 1 to 100 mgm, and preferably about 10 mgm, of salt per gram of cream vehicle. A suitable cream vehicle consists of white petrolatum USP, stearyl alcohol USP, isopropyl myristate, sorbitan monooleate, polyoxyl 40 stearate USP, propylene glycol USP and water, with methylparaben USP 0.3% as a preservative. The proportions are those customary in the art.

In use the burn wounds are cleansed and debrided and the silver phosphanilate cream is applied with sterile, gloved hand. The burn areas should be covered with this cream at all times. The cream is best applied once to twice daily to a thickness of approximately 1/16 inch. Whenever necessary, this cream should be reapplied to any areas from which it has been removed by patient activity. Treatment with this cream should be continued until satisfactory healing has occurred or until the burn site is ready for grafting.

DESCRIPTION OF THE PREFERRED EMBODIMENTS

EXAMPLE 1

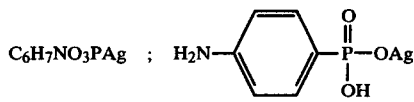

$C_6H_7NO_3PAg$ ;

SYNTHESIS OF MONOSILVER PHOSPHANILATE

To 1.50 g. (0.0087 moles) of Phosphanilic Acid in 525 ml. of Deionized Water at 25° C. was added 1.47 g. (0.0087 moles) of Silver Nitrate previously dissolved in 75 ml. of Deionized Water. The above mixture was added slowly to 600 ml. of Acetone and 1.3 ml. Concentrated Ammonium Hydroxide added. After stirring at 0° C. for one hour, the reaction mixture was filtered and the precipitate was dried in a vacuum oven for 16 hours at 40° C. After drying the material is an off-white to pink, crystalline powder with a yield of 1.90 g., 78% yield; I.R. and elemental analysis were consistent. The product contained 2.48% water (KF).

$C_6H_7NO_3PAg$ Requires:
C-25.74
H-2.53
N-5.00
Ag-38.53
Found:
C-23.50
H-2.36
N-4.72
Ag-37.40

Crystal Form: Diamond shaped and crystal fragments. The crystalline Silver Phosphanilate so formed has been shown to have considerable anti-pseudomonal activity.

EXAMPLE 2

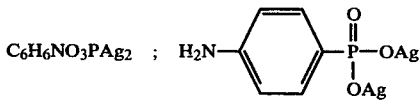

$C_6H_6NO_3PAg_2$ ;

SYNTHESIS OF DISILVER PHOSPHANILATE

To 100 mg. (0.0058 moles) of Phosphanilic Acid in 35 ml. of Deionized Water at 25° C. was added 200 mg. (0.00118 moles) of Silver Nitrate previously dissolved in 5 ml. of Deionized Water. The above mixture was added slowly to 100 ml. of Acetone and two drops of Concentrated Ammonium Hydroxide added. After stirring at 0° C. for one hour, the reaction mixture was filtered and the precipitate was dried in a vacuum oven for 16 hours at 40° C. After drying the material is an off-white to pink, crystalline powder with a yield of 150 mg., 67% yield.

Crystal Form: Crystal fragments.
The product contained 0.40% water (KF)
$C_6H_6NO_3PAg_2$ Requires
C-18.63
H-1.57
N-3.62
Ag-55.77
Found:
C-18.83
H-1.50
N-3.74
Ag-54.00

The crystalline Disilver Phosphanilate so formed has been shown to have considerable anti-pseudomonal activity.

IN VITRO ACTIVITY

Bacteria. The organisms, preponderantly of recent clinical origin, were obtained from numerous sources of broad geographical distribution. Obligate anaerobes were maintained in Egg Meat Medium (Difco); Mycobacterium was stored on Lowenstein Medium [Jensen Modification; Difco). The techniques of storing all other organisms have been described previously (Leitner et al., BL-S640, A Cephalosporin with a Broad Spectrum of Antibacterial Activity: Properties in vitro, Antimicrob. Agents Chemother. 7:298-305 (1975)].

Antibiotic spectrum. The growth-inhibitory activity of the compounds was determined by the antibiotic dilution technique. Procedures were as follows:

Aerobic organisms (excluding Mycobacterium). Except for Haemophilus and Neisseria, the assay was performed in Mueller-Hinton Medium (Difco). For fastidious organisms, i.e., Streptococcus, Listeria, Pasteurella, Bordetella and Vibrio, the medium was supplemented with 4% defibrinated sheep blood. The antibiotic susceptibility of Haemophilus and Neisseria was determined in GC Medium Base (BBL) supplemented with 1% Hemoglobin (BBL) and 1% Isovitalex (BBL).

Overnight broth cultures of an exponentially growing culture (Neisseria) served as the source of inoculum. A volume of approximately 0.003 ml. of the undiluted or diluted culture was applied to the surface of the antibiotic-containing agar plates with the inoculator of Steers et al., An Inocula Replicating Apparatus for Routine Testing of Bacterial Susceptibility to Antibiotics, Antibiot. Chemother. 9:307-311 (1959). Cultures of Neisseria, Streptococcus pneumoniae, *S. viridans* and *S. pyogenes* were used without dilution; those of all other organisms were diluted 100-fold. The inoculum contained about $10^3$ viable cells for Neisseria, $10^5$ for *S. pneumoniae* and *S. pyogenes*, $10^6$ for *S. viridans*, and $10^4$ for all other species. The culture plates were incubated at 37° C. either overnight or for 24 hours (Haemophilus) and the minimum inhibitory concentrations (MIC), i.e., the lowest concentration of antibiotic which prevents visible growth, was recorded.

| | MIC (mcg/ml.) | |
|---|---|---|
| Organism | Monosilver Phosphanilate of Example 1 | Silver Sulfadiazine |
| *Str. pneumoniae* | 32 | 32 |
| | 32 | 32 |
| *Str. pyogenes* | 16 | 32 |
| | 32 | 32 |

|  | MIC (mcg/ml.) | |
|---|---|---|
| Organism | Monosilver Phosphanilate of Example 1 | Silver Sulfadiazine |
| Staph. aureus | 8 | 8 |
|  | 8 | 8 |
| Staph. aureus + 50% serum | 63 | >63 |
|  | 63 | >63 |
| Staph. aureus (Pen-Res) | >125 | >125 |
|  | >125 | >125 |
| Staph. aureus (Meth-Res) | 16 | 8 |
|  | 16 | 8 |
| Str. faecalis | 8 | 8 |
|  | 8 | 8 |
| E. coli | 8 | 16 |
|  | 8 | 16 |
| E. coli | 16 | 8 |
|  | 16 | 8 |
| K. pneumoniae | 16 | 63 |
|  | 16 | 63 |
| K. pneumoniae | 16 | 16 |
|  | 16 | 16 |
| Pr. mirabilis | 8 | 8 |
|  | 8 | 8 |
| Pr. mirabilis | 4 | 8 |
|  | 4 | 8 |
| Pr. morganii | 4 | 8 |
|  | 8 | 8 |
| Pr. rettgeri | 8 | 8 |
|  | 4 | 8 |
| Ser. Marcescens | 4 | 16 |
|  | 4 | 16 |
| Ent. cloacae | 16 | 16 |
|  | 16 | 16 |
| Ent. cloacae | 63 | 32 |
|  | 63 | 32 |
| Ps. aeruginosa | 4 | 16 |
|  | 1 | 16 |
| Ps. aeruginosa | 8 | 8 |
|  | 4 | 8 |
| Ps. aeruginosa | 8 | 63 |
| Ps. aeruginosa | 2 | 8 |
| Ps. aeruginosa | 2 | 16 |
| Ps. aeruginosa | 4 | 16 |

The antibacterial activity of mono- and disilver phosphanilate was also compared with that of silver sulfadiazine against a select group of grampositive organisms, Enterobacteriaceae and *Pseudomonas aeruginosa*. These compounds were tested in a medium essentially free of the phosphanilic acid antagonist thymidine (Mueller-Hinton Broth+0.04 IU/ml thymidine phosphorylase), whereas the data reported above on the activity of monosilver phosphanilate were obtained in nutrient broth without added enzyme.

The table below shows that disilver phosphanilate was marginally more active than monosilver phosphanilate against gram-positive strains and most Enterobacteriaceae. In addition, its antipseudomonal activity was twice that of monosilver phosphanilate.

|  | M.I.C. (mcg/ml) | | |
|---|---|---|---|
| Organism | Monosilver Phosphanilate | Disilver Phosphanilate | Silver Sulfadiazine |
| S. pneumoniae | 8 | 8 | 16 |
| S. pyogenes | 8 | 8 | 16 |
| S. aureus | 8 | 8 | 16 |
| S. aureus (Pen-res.) | 16 | 8 | 16 |
| S. aureus (Meth-res.) | 16 | 8 | 16 |
| S. faecalis | 8 | 4 | 4 |
| E. coli | 4 | 4 | 8 |
| E. coli | 4 | 4 | 8 |
| K. pneumoniae | 16 | 8 | 16 |
| K. pneumoniae | 8 | 4 | 16 |
| P. mirabilis | 8 | 4 | 16 |
| P. vulgaris | 4 | 4 | 4 |
| P. morganii | 4 | 4 | 4 |
| P. rettgeri | 4 | 4 | 4 |
| S. marcescens | 4 | 2 | 4 |
| E. cloacae | 4 | 4 | 8 |
| E. cloacae | 32 | 32 | 8 |
| P. aeruginosa | 4 | 2 | 4 |
| P. aeruginosa | 4 | 2 | 4 |
| P. aeruginosa | 4 | 2 | 8 |
| P. aeruginosa | 4 | 2 | 4 |
| P. aeruginosa | 4 | 2 | 8 |
| P. aeruginosa | 4 | 2 | 8 |

MIC's were determined in Mueller-Hinton Broth+thymidine phosphorylase at 0.04 I.U./ml in every case, except with *S. pneumoniae* and *S. pyogenes* where 2% laked horse blood was added to Mueller-Hinton Broth.

We claim:

1. A silver salt of phosphanilic acid.
2. Monosilver phosphanilate.
3. Disilver phosphanilate.
4. The process for preparing a silver salt of phosphanilic acid which comprises mixing an aqueous suspension of phosphanilic acid with an aqueous solution containing approximately either one or two moles of silver nitrate per mole of phosphanilic acid to form a mixture which is then mixed with a water-miscible organic solvent to precipitate the desired product.
5. The process of claim 4 for preparing a silver salt of phosphanilic acid which comprises mixing an aqueous suspension of phosphanilic acid with an aqueous solution containing approximately either one or two moles of silver nitrate per mole of phosphanilic acid to form a mixture which is then mixed with a water-miscible organic solvent by slow addition to the organic solvent with the addition of a small amount of ammonium hydroxide to precipitate the desired product.
6. The process of claim 4 for preparing a silver salt of phosphanilic acid which comprises mixing at room temperature an aqueous suspension of phosphanilic acid with an aqueous solution containing approximately either one or two moles of silver nitrate per mole of phosphanilic acid to form a mixture which is then mixed with acetone by slow addition of said mixture to the acetone with the addition of a small amount of ammonium hydroxide to precipitate the desired product.
7. The process for preparing monosilver phosphanilate which comprises mixing an aqueous suspension of phosphanilic acid with an aqueous solution containing approximately one mole of silver nitrate per mole of phosphanilic acid to form a mixture which is then mixed with a water-miscible organic solvent to precipitate the desired product.
8. The process of claim 7 for preparing monosilver phosphanilate which comprises mixing an aqueous suspension of phosphanilic acid with an aqueous solution containing approximately one mole of silver nitrate per mole of phosphanilic acid to form a mixture which is then mixed with a water-miscible organic solvent by slow addition to the organic solvent with the addition of a small amount of ammonium hydroxide to precipitate the desired product.

9. The process of claim 7 for preparing monosilver phosphanilate which comprises mixing at room temperature an aqueous suspension of phosphanilic acid with an aqueous solution containing approximately one mole of silver nitrate per mole of phosphanilic acid to form a mixture which is then mixed with acetone by slow addition of said mixture to the acetone with the addition of a small amount of ammonium hydroxide to precipitate the desired product.

10. The process for preparing disilver phosphanilate which comprises mixing an aqueous suspension of phosphanilic acid with an aqueous solution containing approximately two moles of silver nitrate per mole of phosphanilic acid to form a mixture which is then mixed with a water-miscible organic solvent to precipitate the desired product.

11. The process of claim 10 for preparing disilver phosphanilate which comprises mixing an aqueous suspension of phosphanilic acid with an aqueous solution containing approximately two moles of silver nitrate per mole of phosphanilic acid to form a mixture which is then mixed with a water-miscible organic solvent by slow addition to the organic solvent with the addition of a small amount of ammonium hydroxide to precipitate the desired product.

12. The process of claim 10 for preparing disilver phosphanilate which comprises mixing at room temperature an aqueous suspension of phosphanilic acid with an aqueous solution containing approximately two moles of silver nitrate per mole of phosphanilic acid to form a mixture which is then mixed with acetone by slow addition of said mixture to the acetone with the addition of a small amount of ammonium hydroxide to precipitate the desired product.

* * * * *